Jan. 4, 1949. F. TRESCA Plant Pat. 818

LIGUSTRUM PLANT

Filed Dec. 17, 1946

*Inventor:*
*Fuller Tresca,*
*By Cushman, Darby & Cushman*
*Attorneys.*

Patented Jan. 4, 1949

Plant Pat. 818

UNITED STATES PATENT OFFICE

818

LIGUSTRUM PLANT

Fuller Tresca, Jacksonville, Fla.

Application December 17, 1946, Serial No. 716,692

1 Claim. (Cl. 47—59)

The present invention relates to a new and distinct variety of evergreen ligustrum plant, which was initially produced by seeds of the species *Ligustrum japonicum,* and thereafter asexually reproduced, at nurseries in Duval County, near Jacksonville, Florida.

The distinctive characteristics of this new variety of ligustrum plant comprise its somewhat miniature size, as compared with the parent plant of species *Ligustrum japonicum,* and with other varieties of Ligustrum known to me, in the density of its branches and leaves, as well as in the characteristic of the new variety to exhibit a pronounced weeping effect in that its branches, as particularly noticeable on the sides of the plant as naturally grown without trimming, have a pronounced tendency to gracefully recurve downwardly toward their ends.

Specifically, the leaves of this new variety generally are on the order of less than one-half the size of the leaves of Ligustrum varieties known to me, particularly as compared with the leaves of the parent plant of species *Ligustrum japonicum,* and there are many more branches than are found on the common or well-known varieties of Ligustrum, including those of *Ligustrum japonicum.* In addition, my new variety presents a distinctive density in leaf growth, as compared with the common types referred to, the average distance between nodes being approximately ½ inch to ⅝ inch, as compared with 1 inch to 2 inches in the case of the common varieties with which I am familiar, particularly as compared with those of the parent species *Ligustrum japonicum.*

In the drawings, which are photolithographic reproductions of the initially produced new variety:

Figure 1:
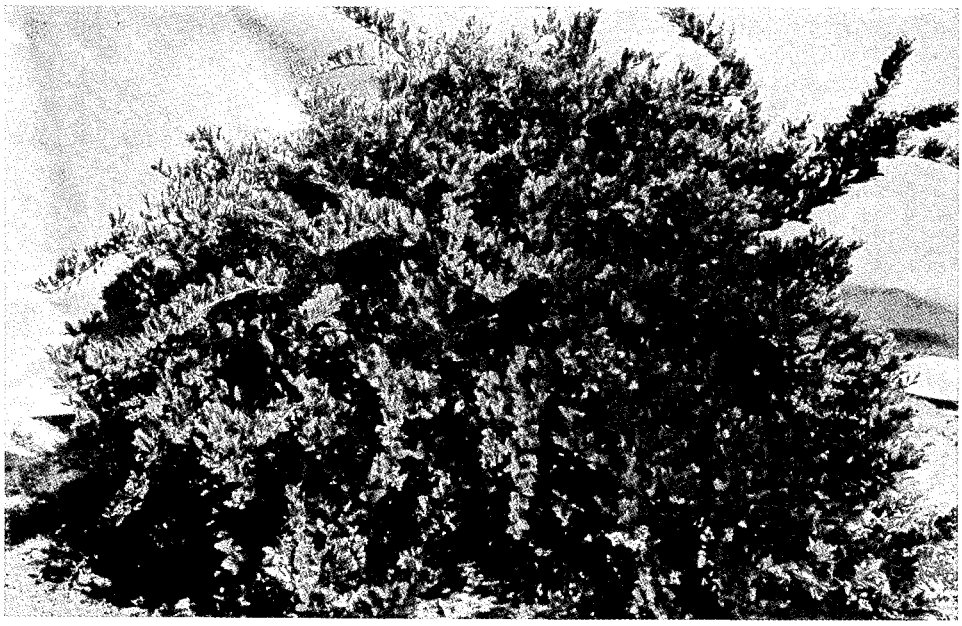
Figure 1 is a photographic side view of the entire plant.
Figure 2:
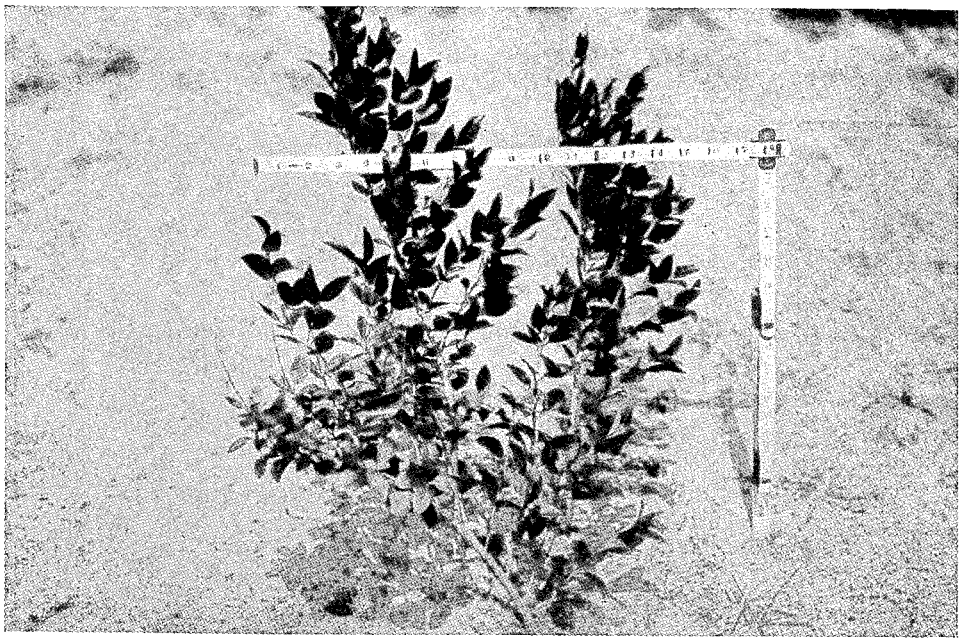
Figure 2 is an enlarged view, as compared with Figure 1, of a branch of the plant of Figure 1, illustrating the relative size and close spacing of the leaves. This branch is not a growing privet, merely being stuck in the ground for support while being photographed.

The history of the development of my new variety follows. About the year of 1937 I undertook the development of improved Ligustrum plants for sale, by planting and selection of superior plants for reproduction.

During the year of 1937, a number of *Ligustrum japonicum* shrubs, of a variety common in this State and well-known to me and which had been propagated for some time in the vicinity of the above-mentioned nursery, were caused to be planted by me on the said nursery property. I took many seeds from these plants and planted them on the same property in the fall of 1938. From these seeds, there grew a considerable number of the common plants which I classify as *Ligustrum japonicum,* but in this group of plants, there was a single plant from the same seeds which I observed to exhibit certain distinctive characteristics described and illustrated herein. These characteristics were observed, and this discovery was first made by me, and I immediately regarded the plant as being superior to the common varieties.

I observed this new plant carefully from time to time, from the time of its discovery in the year succeeding the time of its planting, until the season of 1941–1942. Being impressed with the distinct characteristics of this plant, I decided to determine if they could be perpetuated by vegetative propagation. In approximately December 1941 or in January 1942, I grafted a scion branch of this new plant, so discovered, onto a stalk of *Ligustrum amurense.*

During the season 1942–1943, the particular plant which was grafted as referred to above commenced to demonstrate the distinctive characteristics of the new variety as described and illustrated herein, and confirmed my belief that this new variety would reproduce its distinctive features, by vegetative propagation. Continued observation of the propagated plant fulfilled expectations, and like the initially seed produced parent plant, it grew to a relatively miniature height, and exhibited the other distinctive characteristics mentioned herein.

At about the time of the first grafting from the initially seed produced plant of the new variety, as referred to above, and to make my test of perpetuability certain, I cause additional graftings therefrom to be made on other stalks of *Ligustrum amurense,* to the number of approximately thirty-five small plants, and found that all of these propagations developed into plants having the distinctive characteristics of the new variety as described herein.

I have continuously observed the growth of these propagations up to the present time, and have been careful to insure that they do not receive any unusual treatment or protection in cultivation. My continued observations of these propagations have indicated that they are as free of disease and are as sturdy as the conventional Ligustrum varieties. In fact, in unusually cold weather for this area of Florida in November 1945, I found that the propagation of the new variety was able to resist an unusually low temperature of 17° better than the adjacent plants of the common *Ligustrum japonicum* variety.

As referred to above, the new variety is characterized by a low but wide compact habit of growth with relatively long and flexible gracefully arching or recurving branches, which rise upwardly from their nodes and then arch and recurve downwardly, giving a weeping effect near or toward their ends. The plant has attained a height of approximately four feet, as compared with the greater height of adjacent plants of the common variety planted at the same time, the width of the plant being generally greater than its height. The leaves are smaller than those of typical Ligustrum, generally averaging less than 1½ inches in length and approximately 1 inch or less in width. The leaves are of a rich, glossy green color on the upper side and of a pale, waxy green appearance on the underside. The leaves vary in shape from oval, ovate or nearly circular to broadly obovate. The tips of the leaves are rounded or blunt-pointed. In general, the nodes are relatively more closely spaced and hence the leaves are more numerous than on typical plants of the species. Numerous short leafy branches arise from many of the nodes, adding to the density of the growth. The flower clusters are similar to those on common varieties of the species as referred to, except that they are generally shorter and more compact.

My new variety differs from all varieties of *Ligustrum japonicum* or other species known to me in its low, densely-leafy form and in the gracefully arching or recurving habit of its branches.

Having described my invention or discovery as completely as it is reasonably possible for me to do, I claim:

A new and distinct variety of Ligustrum plant substantially as herein disclosed, characterized by its generally low wide outline or configuration, by the greater density of its leaves and branches as compared with other varieties of *Ligustrum japonicum,* resulting from the presence of a substantially greater and more closely spaced number of branches and leaves of smaller size, and by the gracefully arching and downwardly recurving habit of its branches, whereby an overall weeping appearance is presented.

FULLER TRESCA.

No references cited.